United States Patent
Acquati et al.

(10) Patent No.: US 6,528,280 B1
(45) Date of Patent: Mar. 4, 2003

(54) PROCESS FOR THE PREPARATION OF DERIVATIVES OF RUSCUS ACULEATUS STEROID GLYCOSIDES

(75) Inventors: Walter Acquati, Milan (IT); Cesare Ponzone, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/979,141

(22) PCT Filed: May 16, 2000

(86) PCT No.: PCT/EP00/04794

§ 371 (c)(1),
(2), (4) Date: Jan. 15, 2002

(87) PCT Pub. No.: WO00/73489

PCT Pub. Date: Dec. 7, 2000

(30) Foreign Application Priority Data

Jun. 1, 1999 (IT) .......................................... MI99A1223

(51) Int. Cl.[7] ........................... C12P 33/20; C12P 33/00
(52) U.S. Cl. ........................................... 435/53; 435/52
(58) Field of Search ............................................ 435/53

(56) References Cited

FOREIGN PATENT DOCUMENTS

| FR | 2 104 911 | 4/1972 |
| GB | 1 380 253 | 1/1975 |

OTHER PUBLICATIONS

Computer Caplus Abstract 1976:87880 Perepelitsa et al Prikl.Biokhim Mik (1975)11 (6) 901–5.*
Computer Caplus Abstract 1975:528650 Perepelitsa et al Khim Prir.Soedin (1975) 11 (2) 260–1.*
ATCC Catalogue Bacteria & Bacteriophages 18th Ed 1993 p. 544.*
Computer Pascal Abstract 1994–0473378 Ray et al Jour Microbial Biotech (1993) 8(2) 84–95.*
Computer Pascal Abstract 1985–0261580 Okada Agric. & Biol. Chem. (1985) 49 (5) 1257–1265.*

* cited by examiner

Primary Examiner—Herbert J. Lilling
(74) Attorney, Agent, or Firm—Pennie & Edmonds LLP

(57) ABSTRACT

A process for the preparation of desglucodesrhamnoruscin which comprises the hydrolysis of *Ruscus Aculeatus* steroid glycosides (ruscosaponins) through fermentation of a substrate containing said glycosides by means of fungi of the *aspergillus niger* species.

20 Claims, No Drawings

PROCESS FOR THE PREPARATION OF DERIVATIVES OF RUSCUS ACULEATUS STEROID GLYCOSIDES

This application is a 321 of PCT/EP00/04794 filed May 16, 2000, and Italy MI99A1223 filed Jun. 1, 1999.

TECHNICAL FIELD

The present invention relates to a process for the preparation of derivatives of *Ruscus Aculeatus* steroid glycosides (ruscosaponins).

More particularly, the invention relates to the preparation of desglucodesrhamnoruscin by hydrolysis of ruscoside and/or desglucoruscoside through the fermentation route.

BACKGROUND OF THE INVENTION

Desglucorhamnoruscin and the corresponding free aglycons, ruscogenin and neoruscogenin, which can be easily obtained from desglucodesrhamnoruscin by acid hydrolysis, are valuable pharmaceutical active principals having antiinflammatory and connective-protecting activities.

The chemical preparation of said active principles starting from ruscoside or desglucoruscoside is however problematic, since it requires drastic conditions, such as hydrolysis with strong acids, and complex operative steps, which yield a very heterogeneous mixture of intermediates and products.

It would therefore be highly desirable to provide a process for the preparation of desglucodesrhamnoruscin, which overcomes the drawbacks mentioned above connected with the known chemical processes.

SUMMARY OF THE INVENTION

The present invention meets such a need, by providing a process for the preparation of desglucodesrhamnoruscin which comprises the hydrolysis of *Ruscus aculeatus* steroid glycosides (ruscosaponins) through fermentation of a substrate containing said glycosides by means of fungi of the *aspergillus niger* species.

A culture broth is typically used as a nutrient complex substrate.

Fermentation is generally carried out at a temperature of 25–30° C., preferably 27° C., under stirring and aeration so as to attain a pO2 higher than or equal to 50%.

The concentration of the starting steroid glycosides usually ranges from 5 to 15% w/v, preferably from 8 to 10% w/v and the pH of the culture broth ranges from 4 to 6, preferably 4.5–5.5.

DETAILED DESCRIPTION OF THE PREFERRED EMBODIMENTS

The biotechnological process of the present invention allows to carry out the whole reactions sequence in a single fermentation step, in that the microorganism, selected with suitable microbiological techniques, is capable of expressing the necessary enzymatic activities for operating all the transformation sequential reactions, from the starting complex heteroglycoside to the monoglycoside or the final aglycone. Said hydrolase transformations comprise in fact a sequence of β-glucosidase, α-rhamnosidase reactions on the intermediates which are successively released during the process. A further α-arabinosidase reaction allows to obtain the free aglycone (ruscogenin).

Said approach is quite novel, in that no applicative examples of said procedure for the preparation of said products can be found in literature.

The microorganisms suitable for carrying out the transformations involved are obtained by selection on synthetic or semi-synthetic media, added with the same substrates to be transformed, in addition to or in place of the conventional carbon sources (glucose, saccharose, and the like). The concerned substrates (ruscoside, desglucoruscoside) can be added in this case in even high concentrations, e.g. 90–100 g/L. The agarized isolation media comprise the usual formulations for microbiology, such as Malt Agar and Czapek Agar, or similar formulations, wherein the nitrogen source is represented by peptones, urea, ammonium nitrate, and the like, whereas the conventional carbon source (glucose, saccharose) has been substituted or supplemented by ruscoside or desglucoruscoside. Said media can be further added with mineral salts of potassium, magnesium, manganese, zinc etc., such as phosphates, sulfates and/or chlorides. The pH of the isolation media can range from 4 to 6, preferably from 4.5 to 5.5.

The microorganisms suitable to the required biotrasformations are recovered by scalar dilution and plating of aqueous suspensions of samples of soil, humus, vegetable extracts and other similar organic sources.

The microbial cultures selected as described above are isolated in microbiology test-tubes containing the same culture media and used for the biotransformation of ruscoside and desglucoruscoside, added in high concentrations (to 100 g/L) to liquid culture media containing the same nitrogen sources as used in the isolation media, such as urea or peptone, with the addition of phosphates and other mineral salts, as described above, at pH ranging from 4 to 6, preferably 4.5÷5.5.

Following the procedures described it has been found that selected cultures of *Aspergillus niger* are capable of transforming ruscoside and desglucoruscoside into desglucodesrhamnoruscin, a direct precursor of ruscogenins, by a sequence of enzymatic β-glucosidase and α-rhamnosidase reactions.

A subsequent α-arabinosidase reaction provides the saponin in the aglyconic form (ruscogenin-neoruscogenin).

The selected culture is capable of operating said transformations growing in controlled (thermostatic) conditions, at optimal temperatures ranging from 25° C. to 30° C., under stirring on a rotatory shaker (200÷300 rpm). Said fermentation can also be carried out in a suitable bioreactor, at different scale levels, for the industrial production of the desired saponin derivatives.

The microorganisms used for said biotransformation are capable of steadily maintaining the catalytic activity, even for repeated fermentation cycles, in batch or continuous processes.

The present process provides important advantages, such as less complex the steps for the separation and recovery of the product, and is also easy to carry out as well as cost-saving.

The selected microorganisms can be frozen for the to long-term storage, in suspensions enriched with cryopreservatives, such as glycerol, peptone and the like, at temperatures ranging from −80° C. to −196° C. (in liquid nitrogen), or subjected to freeze-drying treatments.

The progress of the bioconversion can be monitored by TLC and HPLC analysis on the culture broth, using the following analytical methods:

TLC Analysis
   Silica gel plates 60 F250 Merck
   Eluents:
      A) Ethyl acetate-Methanol 9:1
      B) Ethyl acetate-Methanol-Water 100:15:10.
   Detection: reaction with 10% sulfuric acid and heating to 120° C. for 5 minutes, then visible and UV detection.
HPLC Analysis
   Column: Supelcosil LC18, 250×4,6 mm, 5 μm
   Eluent: acetonitrile-water 60:40
   Wavelength: 200 nm
   Injection volume: 10 μl
   Flow: 1 mL/min.

The final biotransformation products, such as desglucodesrhamnoruscin, can be recovered by extraction of the culture broth with n-butanol, subsequent purification steps with chlorinated solvents (such as trichloroethane) and silica gel chromatography. Finally, the product can be crystallized from different solvents, such as isopropanol, ethyl acetate, chloroform, acetone, methanol. In addition to the main product, desglucodesrhamnoruscins esterified at C-2', for example with 2-hydroxy-3-methylpentanoic acid, can be obtained.

The saponins in the aglyconic form (ruscogenins) are obtained by acid hydrolysis of the fermentation products described above.

The following examples disclose the invention in greater detail.

EXAMPLE 1

2 Flasks of culture medium (Malt Broth, 250 mL per flask) are inoculated with spores from a culture of *Aspergillus niger* on Malt Agar, obtained by selection on Modified Agar malt medium (added with 2% ruscoside). The flasks are incubated for 48 hours at +27° C., on an orbital stirrer at 250 rpm. After incubation, the preculture is transferred into the bioreactor, containing about 7 L of sterile production broth RO90, having the following composition (values referred to one liter of deionized water) Ruscoside Dry extract (g 90), Urea (g 1), Peptone (g 1), $MgSO_4.7H_2O$ (g 5), KCl (g 1,5), $KH_2PO_4$ (g 1), $MnSO_4.H_2O$ (g 0.2), $ZnSO_4.7H_2O$ (g 0.1) antifoam P2000 (mL 1,5), at about pH 5.

The fermentation is carried out on the basis of the dissolved oxygen percentage ($pO_2$), progressively increasing the stirring rate and the air flow, to obtain a $PO_2$ value higher than 50%. The progress of the bioconversion is monitored by HPLC and TLC analysis. After 5 day incubation at +27° C. the fermentation is over. TLC and HPLC analysis of the broth show that ruscoside has disappeared while desglucodesrhamnoruscin is present as main product, with ruscogenins traces.

The culture broth is exhaustively extracted with n-butanol. The butanol extract is concentrated to dryness under vacuum at +60° C., redissolved in 70% methanol and back-extracted with trichloroethane. The chlorinated solution is concentrated Lo a solid under vacuum. After redissolution in a chloroform-methanol mixture, the product is purified by column chromatography (Kieselgel, Merck), with ethyl acetate-chloroform 9:1 as eluent. The fractions are checked by TLC or HPLC analysis. The purified product fraction is concentrated under vacuum, then redissolved in acetone and crystallized. A further crystallization from methanol yields about 7 g of product, identified by spectroscopic analysis as desglucodesrhamnoruscin. In addition to the main product, a desglucodesrhamnoruscin esterified at C-2' with 2-hydroxy-3-methylpentanoic acid is obtained in lower amount (about 800 mg).

Acid hydrolysis of the Fermentation products described above yields the saponins in the aglyconic form (ruscogenins).

EXAMPLE 2

Operating in a fermenter as described in example 1, a first biotransformation cycle is carried out, after that 90% of the culture broth is taken to be extracted for obtaining the product; the remaining 10% fermentation broth is added in the fermenter with fresh RO90 medium to a final volume of about 7 L. This second fermentation cycle is carried out with the same parameters and analytical controls as described above. After about 5 day incubation at +27° C. the fermentation is completed.

The culture broths from the two fermentation cycles are treated as described in example 1, for the extraction and recovery of the product. At the end of the final step, about 14 g of desglucodesrhamnoruscin are obtained.

What is claimed is:

1. A method for preparing desglucodesrhamnoruscin which comprises hydrolyzing *Ruscus aculeatus* steroid glycosides by fermenting a culture broth containing said *Ruscus aculeatus* steroid glycosides with a fungi of the *Aspergillus niger* species to provide desglucodesrhamnoruscin, wherein the fermenting is conducted at a temperature of from 25–30° C., with stirring, and with aeration to provide an oxygen percentage of at least 50 percent.

2. The method of claim 1, wherein the temperature is 27° C.

3. The method of claim 1, wherein the concentration of the *Ruscus aculeatus* steroid glycosides in the composition of from 5 to 15 w/v percent.

4. The method of claim 3, wherein the concentration of the *Ruscus aculeatus* steroid glycosides in the composition is from 8 to 10 w/v percent.

5. The method of claim 1, wherein the pH of the composition is from 4 to 6.

6. The method of claim 5, wherein the pH of the composition is from 4.5 to 5.5.

7. The method of claim 1, wherein the stirring is performed with a rotary shaker operated at from 200 to 300 rpm.

8. The method of claim 1, further comprising recovering the desglucodesrhamnoruscin from the composition.

9. The process of claim 8, further comprising recovering the desglucodesrhamnoruscin from the composition by extracting the composition with n-butanol to provide an n-butanol extract and removing the n-butanol to provide a further purified desglucodesrhamnoruscin.

10. The method of claim 9, further comprising:
   redissolving the crude desglucodesrhamnoruscin in 70 percent aqueous methanol to provide an aqueous methanol solution of desglucodesrhamnoruscin;
   extracting the aqueous methanol solution of desglucodesrhamnoruscin with trichloroethane to provide a trichloroethane solution of desglucodesrhamnoruscin;
   removing the trichloroethane from the trichloroethane solution of desglucodesrhamnoruscin to provide partially purified desglucodesrhamnoruscin;
   dissolving the partially purified desglucodesrhamnoruscin in a solution of chloroform and methanol to provide a chloroform-methanol solution of desglucodesrhamnoruscin;

placing the partially purified chloroform-methanol solution of desglucodesrhamnoruscin on a Kieselgel column and eluting the desglucodesrhamnoruscin with a solution of acetone and chloroform (9:1) to provide an acetone-chloroform solution of substantially pure desglucodesrhamnoruscin;

removing the acetone and chloroform form the acetone-chloroform solution of substantially pure desglucodesrhamnoruscin to provide substantially pure desglucodesrhamnoruscin; and recrystallizing the substantially pure desglucodesrhamnoruscin from acetone to provide purified desglucodesrhamnoruscin.

11. The method of claim 10, further comprising recrystallizing the desglucodesrhamnoruscin from methanol.

12. The method of claim 11, wherein the concentration of the *Ruscus aculeatus* steroid glycosides in the culture broth of from 5 to 15 w/v percent.

13. The method of claim 12, wherein the concentration of the *Ruscus aculeatus* steroid glycosides in the culture broth is from 8 to 10 w/v percent.

14. The method of claim 11, wherein the pH of the culture broth is from 4 to 6.

15. The method of claim 14, wherein the pH of the culture broth is from 4.5 to 5.5.

16. The method of claim 11, wherein the stirring is performed with a rotary shaker operated at from 200 to 300 rpm.

17. The method of claim 1, further comprising recovering the desglucodesrhamnoruscin from the culture broth.

18. The method of claim 17, wherein the desglucodesrhamnoruscin is recovered from the composition by extracting the culture broth with n-butanol to provide an n-butanol extract and removing the n-butanol to provide further purified desglucodesrhamnoruscin.

19. The method of claim 18, further comprising:

redissolving the further purified desglucodesrhamnoruscin in 70 percent aqueous methanol to provide an aqueous methanol solution of desglucodesrhamnoruscin;

extracting the aqueous methanol solution of desglucodesrhamnoruscin with trichloroethane to provide a trichloroethane solution of desglucodesrhamnoruscin;

removing the trichloroethane from the trichloroethane solution of desglucodesrhamnoruscin to provide partially purified desglucodesrhamnoruscin;

dissolving the partially purified desglucodesrhamnoruscin in a solution of chloroform and methanol to provide a chloroform-methanol solution of desglucodesrhamnoruscin;

placing the partially purified chloroform-methanol solution of desglucodesrhamnoruscin on a Kieselgel column and eluting the desglucodesrhamnoruscin with a solution of acetone and chloroform (9:1) to provide an acetone-chloroform solution of substantially pure desglucodesrhamnoruscin;

removing the acetone and chloroform form the acetone-chloroform solution of substantially pure desglucodesrhamnoruscin to provide substantially pure desglucodesrhamnoruscin; and recrystallizing the substantially pure desglucodesrhamnoruscin from acetone to provide purified desglucodesrhamnoruscin.

20. The method of claim 19, further comprising recrystallizing the desglucodesrhamnoruscin from methanol.

\* \* \* \* \*

UNITED STATES PATENT AND TRADEMARK OFFICE
CERTIFICATE OF CORRECTION

PATENT NO.    : 6,528,280 B1                                              Page 1 of 1
DATED         : March 4, 2003
INVENTOR(S)   : Walter Acquati and Cesare Ponzone It is certified that error appears in the above-identified patent and that said Letters Patent is hereby corrected as shown below:

Column 4,
Lines 35-36, replace "composition of" with -- culture broth is --.
Lines 38, 40-41 and 42-43, replace "composition" with -- culture broth --.

Signed and Sealed this

Fifteenth Day of July, 2003

JAMES E. ROGAN
*Director of the United States Patent and Trademark Office*